United States Patent
Esteve et al.

(10) Patent No.: US 8,539,946 B2
(45) Date of Patent: Sep. 24, 2013

(54) DRY POWDER INHALER

(75) Inventors: Victor Esteve, Sao Paulo (BR); Achim Kreim, Fränkisch-Crumbach (DE)

(73) Assignee: Eric Zembrod, Boituva-SP (BR)

(*) Notice: Subject to any disclaimer, the term of this patent is extended or adjusted under 35 U.S.C. 154(b) by 853 days.

(21) Appl. No.: 12/224,167

(22) PCT Filed: Feb. 19, 2007

(86) PCT No.: PCT/EP2007/001408
§ 371 (c)(1),
(2), (4) Date: Jun. 9, 2009

(87) PCT Pub. No.: WO2007/098870
PCT Pub. Date: Sep. 7, 2007

(65) Prior Publication Data
US 2011/0120463 A1    May 26, 2011

(30) Foreign Application Priority Data

Feb. 24, 2006 (DE) .................. 10 2006 010 089

(51) Int. Cl.
*A61M 16/00* (2006.01)
(52) U.S. Cl.
USPC ............................ 128/203.15; 128/203.21
(58) Field of Classification Search
USPC .............. 128/203.15, 203.21–203.24, 207.18
See application file for complete search history.

(56) References Cited

U.S. PATENT DOCUMENTS

| 3,906,950 | A | 9/1975 | Cocozza |
| 5,372,128 | A | 12/1994 | Haber |
| 7,448,379 | B2 * | 11/2008 | Yamashita et al. ....... 128/203.15 |
| 7,861,712 | B2 * | 1/2011 | Jones et al. ............. 128/203.15 |
| 2003/0101995 | A1 * | 6/2003 | Yamashita et al. ....... 128/203.15 |
| 2005/0238708 | A1 * | 10/2005 | Jones et al. ................... 424/451 |

FOREIGN PATENT DOCUMENTS

| DE | 27 04 574 | 8/1977 |
| DE | 196 37 125 | 3/1998 |
| DE | 197 04 849 | 8/1998 |
| DE | 694 21 415 | 2/2000 |
| DE | 695 28 237 | 1/2003 |
| DE | 697 20 415 | 11/2003 |
| DE | 602 00 547 | 6/2005 |
| DE | 10 2004 019 566 | 11/2005 |
| EP | 0 406 893 | 1/1991 |

(Continued)

OTHER PUBLICATIONS

Office Action from Canadian Patent Office regarding equivalent application.

*Primary Examiner* — Lynne Anderson
(74) *Attorney, Agent, or Firm* — B. Aaron Schulman, Esq.; Stites & Harbison PLLC

(57) ABSTRACT

The invention relates to a dry powder inhaler, having a base housing, having a capsule receptacle for a capsule containing dry powder, having at least one needle- or blade-like opening means, movably arranged in relation to the base housing, for opening the capsule, and having a mouthpiece, through which the dry powder from an opened capsule can be inhaled. The invention is distinguished in that the opening means are fastened on the mouthpiece, and that the mouthpiece can be moved in respect to the base housing out of a normal position into an opening position which opens the capsule.

18 Claims, 4 Drawing Sheets

(56) References Cited

FOREIGN PATENT DOCUMENTS

| EP | 0 491 426 | 6/1992 |
| EP | 0 666 085 | 8/1995 |
| EP | 0 950 423 | 10/1999 |
| EP | 1 082 971 | 3/2001 |
| EP | 1 350 532 | 10/2003 |

* cited by examiner

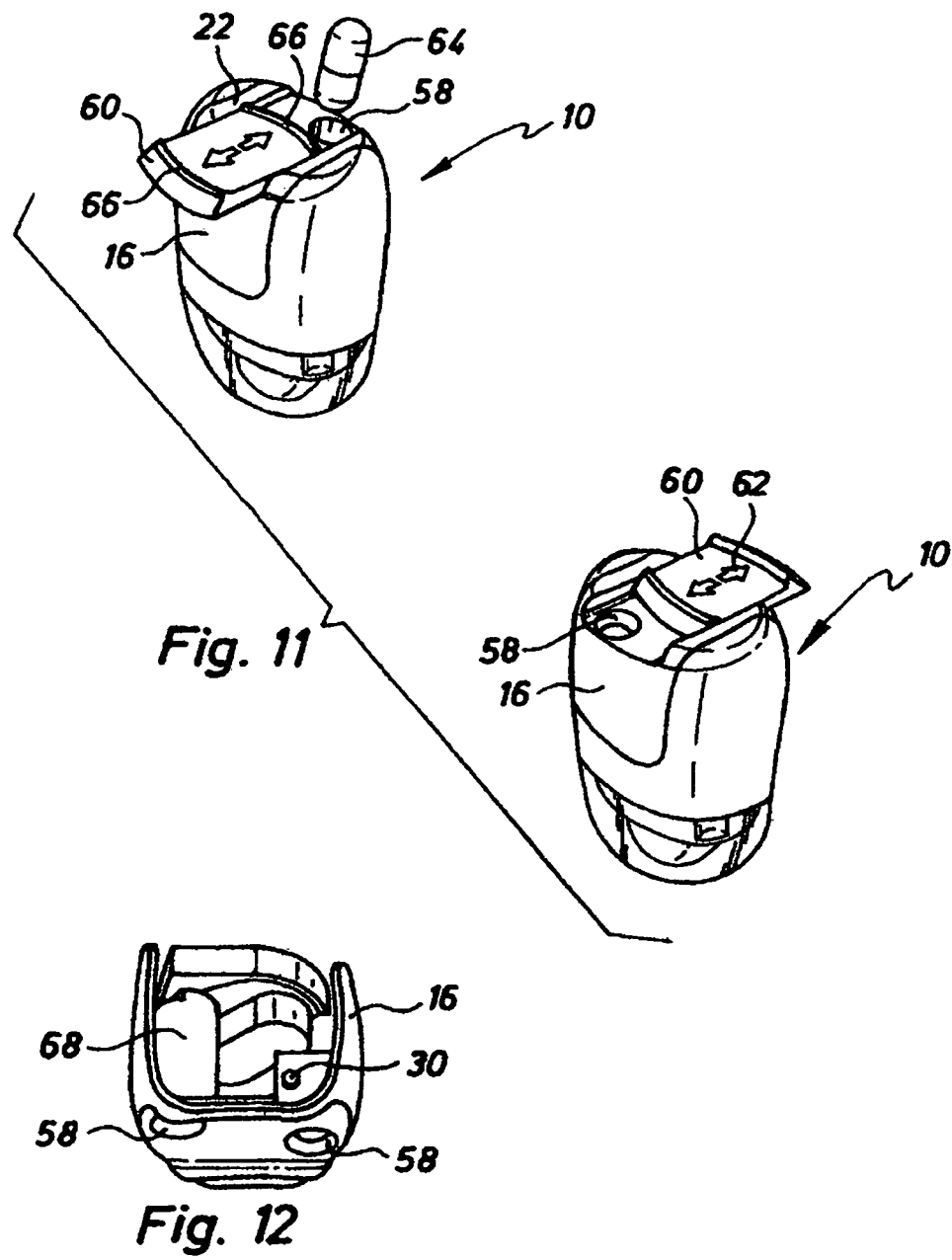

DRY POWDER INHALER

This application is the national stage of PCT/EP2007/001408 filed on Feb. 19, 2007 and claims Paris convention priority of DE 10 2006 010 089.1 filed Feb. 24, 2006.

BACKGROUND OF THE INVENTION

The invention relates to a dry powder inhaler, having a base housing, having a capsule receptacle for a capsule containing dry powder, having at least one needle- or blade-like opening means, movably arranged in relation to the base housing, for opening the capsule, and having a mouthpiece, through which the dry powder from an opened capsule can be inhaled.

Such a dry power inhaler is known, for example, from EP-A-1 270 034, of from USP-A-2003/0000523.

In connection with such known inhalers, separate actuating means, which are fixedly connected with the opening means, are provided, and are pressed into the base housing for opening the capsule.

It is intended by means of the present invention to find an advantageous alternative solution as to how capsules can be opened in an advantageous manner.

SUMMARY OF THE INVENTION

To this end, the invention provides that the opening means are fastened on the mouthpiece, and that the mouthpiece can be moved in respect to the base housing out of a normal position into an opening position which opens the capsule. By means of this it is advantageously achieved that no separate actuating means for opening the capsule need to be provided. In accordance with the invention the mouthpiece, which is an indispensable part of an inhaler, is given an additional function: based on its mobility and on the opening means arranged on it, it is used for opening the capsule.

For bringing the mouthpiece back into its normal position again, it can be provided in accordance with the invention that at least one spring element is provided between the housing and the mouthpiece. Therefore, when moving or pushing the mouthpiece out of the normal position into the opening position, it is necessary to make a movement force available which is greater than the spring force with which the mouthpiece is maintained in the normal position. In accordance with the invention one spring element or several spring elements can be provided. The provision of several spring elements, for example several helical springs arranged parallel with each other or coaxially inside each other, can have the advantage that a more uniform prestressing force is made available, by means of which tilting or jamming of the mouthpiece in the course of being changed from the opening position into the normal position is counteracted.

From the normal position, the mouthpiece is advantageously moved into the opening position in the axial direction in respect to the center longitudinal axis of the mouthpiece, or of the base housing. The mouthpiece can in particular be arranged in such a way that at least portions of it are introduced into the base housing in the course of being transferred from the normal position into the opening position.

It can be provided in accordance with an advantageous further development of the invention that at least one needle extending in the longitudinal direction of the mouthpiece is used as the opening means. In this case the needle can be arranged in such a way that in the normal position of the mouthpiece the needle does not enter into the capsule receptacle. When pushing down the mouthpiece, at least the tip of the needle extends into the capsule receptacle, into which the suitable capsule can be inserted.

A substantially sleeve-like intermediate element at the base housing can be used for guiding the mouthpiece from its normal position into the opening position. The mouthpiece is advantageously guided over the entire movement track of the mouthpiece. In this case the sleeve-like intermediate element is advantageously designed in such a way that in the process of inhaling the dry powder it conducts the dry powder from the capsule receptacle to the mouthpiece. For this purpose the intermediate element can have a sieve-like structure on the side facing the capsule receptacle, which during inhalation prevents the capsule receptacle from getting into the intermediate element, or into the mouthpiece. The sieve-like structure accordingly holds the capsule back inside the capsule receptacle.

By means of the dry powder inhaler in accordance with the invention it is furthermore intended to achieve that the insertion of the capsule can take place in an advantageous manner. This is achieved in that in accordance with the invention the capsule receptacle is arranged to be pivotable in relation to the base housing in such a way, that at least portions of it can be pivoted out of the base housing for introducing a capsule. Thus, an easy and user-friendly introduction of the capsule into the capsule receptacle can take place, based on the pivotable arrangement of the capsule receptacle.

In this connection it is conceivable that the pivot axis around which the capsule receptacle is pivotable, extends perpendicularly in relation to the center longitudinal axis of the mouthpiece or of the base housing. Accordingly, the capsule receptacle is then pivoted laterally out of the base housing.

Furthermore, it has been advantageously provided that the pivot axis, around which the capsule receptacle can be pivoted, is arranged offset in relation to the center longitudinal axis of the mouthpiece or of the base housing. Because of this non-centered arrangement of the pivot axis it has been achieved that the capsule receptacle is easily accessible even at a small opening angle.

For the pivotable arrangement of the capsule receptacle, on its side facing away from the mouthpiece, the base housing can provide a pivoting element comprising or supporting the capsule receptacle which, in its not pivoted-out normal position, terminates flush, at least to a large extent, with the exterior of the base housing. By means of this it is achieved that, in the normal position of the pivoting element, the pivoting element advantageously fits into the base housing.

The pivoting element as such can have a U-shaped exterior contour in a lateral view, which can extend from the front over the underside as far as the back of the base housing. This has the advantage that pivoting-out of the pivoting element can take place, for example, by grasping the front and back of the pivoting element with two fingers. To this extent the pivoting element can be pivoted in a simple way from the normal position into the pivot position and thereafter, following the insertion of the capsule, can be pivoted back out of the pivoted position into the normal position.

In this case the capsule receptacle is advantageously arranged between the two U-legs of such a pivoting element. Then the capsule receptacle can be embodied as one piece with the pivoting element, or can be fastened on the pivoting element as a separate component.

The capsule receptacle as such advantageously has a depression, which is embodied to be slightly larger than the capsule, and which is followed by surfaces extending in a funnel-shape toward the depression. By means of this it is achieved that in the course of inserting the capsule into the capsule receptacle the former automatically takes up the intended position in the depression. When opening the capsule, the capsule is located in the depression; therefore no lateral excursion of the capsule can take place when the opening means impinges on the capsule.

Advantageously the longitudinal axis of the depression of the capsule receptacle extends obliquely in relation to a center longitudinal plane of the base housing. In this case the longitudinal axis of the depression can enclose an angle of approximately 45° with the center longitudinal plane of the broad side of the base housing. Such an angle has the advantage that, with the capsule receptacle pivoted-up, the capsule finds its own way into the depression. Furthermore, the capsule can be removed in a simple way out of the depression after the inhaler has been used.

Moreover, the capsule receptacle can be delimited by a substantially perfectly circular upper edge. By means of this it is possible to make available a definite termination, or connection with the underside of the sleeve-like intermediate element which faces the capsule receptacle. Moreover, a suction inlet for suctioning in the course of inhalation can be provided in the area of the upper edge. Here, the suction inlet is advantageously arranged perpendicularly in relation to the center longitudinal axis of the housing, or respectively of the mouthpiece.

In accordance with the invention it is furthermore advantageous if the capsule receptacle has a storage space for the storage of capsules. It is possible by means of this to carry along a certain reserve of capsules in the inhaler. It is conceivable here that, when the capsule receptacle is pivoted-out, the storage space is accessible for the introduction of capsules to be stored, or the removal of stored capsules and, when the capsule receptacle is pivoted-in, it is not accessible. When transporting the inhaler with the capsule receptacle closed, the capsules are stored, safe against loss, in the storage space.

Further details and advantageous embodiments of the invention can be taken from the dependent claims and the following description, in which two exemplary embodiments, which are represented in the drawings, are described in greater detail and explained.

BRIEF DESCRIPTION OF THE DRAWING

Shown are in.

DESCRIPTION OF THE PREFERRED EMBODIMENT

Figure 1:
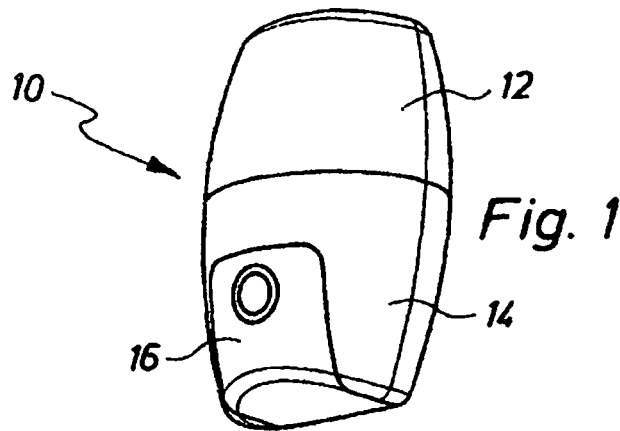
FIG. 1, a perspective plan view of a dry powder inhaler in accordance with the invention with the cover placed thereon, FIG. 2, a front view of the inhaler in accordance with FIG. 1 without cover, FIG. 3, a lateral view of the inhaler in accordance with FIG. 1.

The dry powder inhaler 10 represented in FIG. 1 is comprised of a cover 12, a base housing 14 and a pivoting element 16 pivotably arranged on the base housing.

Figure 2:
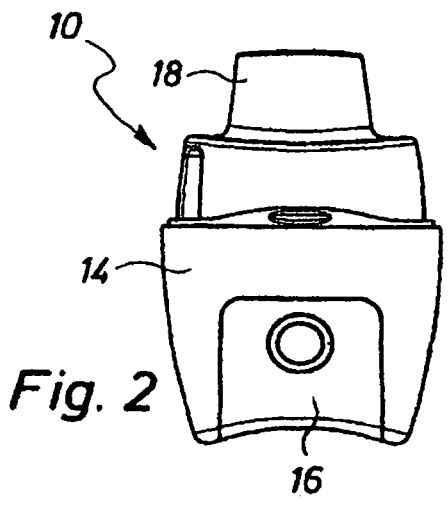
Figure 3:
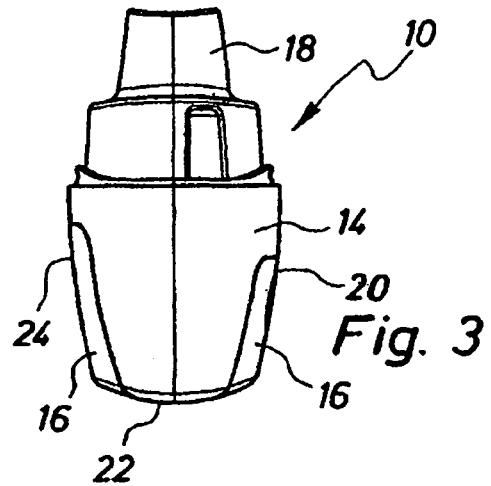

The inhaler 10 in accordance with FIG. 1 is represented without the cover 12 in FIGS. 2 and 3. A mouthpiece 18 is visible, which extends in the longitudinal direction of the inhaler 10 and is embodied to be hollow, through which the dry powder in an open capsule present in the inhaler can be inhaled.

As becomes clear in particular from FIG. 3, the pivoting element 16 extends from the front side 20 of the base housing over an underside 22 of the base housing as far as the back 24 of the base housing. Accordingly, the pivoting element 16 is embodied in a U-shape in a lateral view. In the normal position of the pivoting element represented in FIGS. 1 to 3, it terminates flush to a large extent with the exterior of the base housing 14.

Figure 4:
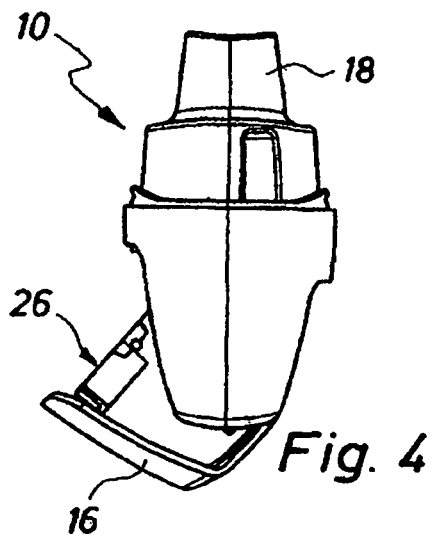
FIG. 4, a plan view of the inhaler in accordance with FIG. 3 with the capsule receptacle pivoted open, FIG. 5, a perspective plan view of FIG. 4, FIG. 6, a view from above on the inhaler in accordance with FIG. 1, FIG. 7, a section along the line A-A in FIG. 6, FIG. 8, a section along the line D-D in FIG. 6, FIG. 9, a section along the line C-C in FIG. 6, FIG. 10, the sectional view in accordance with FIG. 9 with the mouthpiece pressed down, FIG. 11, a view from above on the underside of the turned-over inhaler, and FIG. 12, the pivoting element with the cap pulled off.
Figure 5:
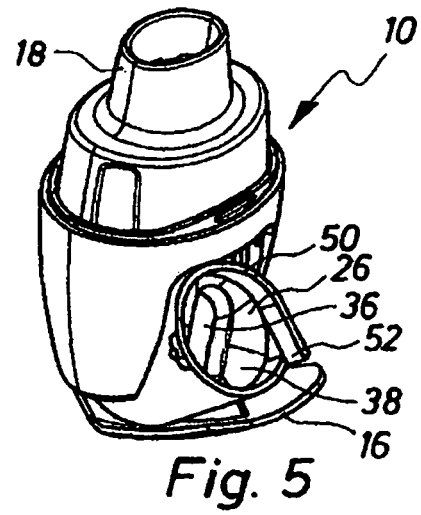

In FIGS. 4 and 5 the pivoting element 16 is represented in a pivoted position in which it has been pivoted out of the base housing 14. A capsule receptacle 26 arranged on the pivoting element 16 is accessible in the pivoted position. A dry powder capsule can be inserted into the capsule receptacle 26. Following the insertion of the capsule, the pivoting element is pivoted back again into its normal position.

Figures 7, 8:
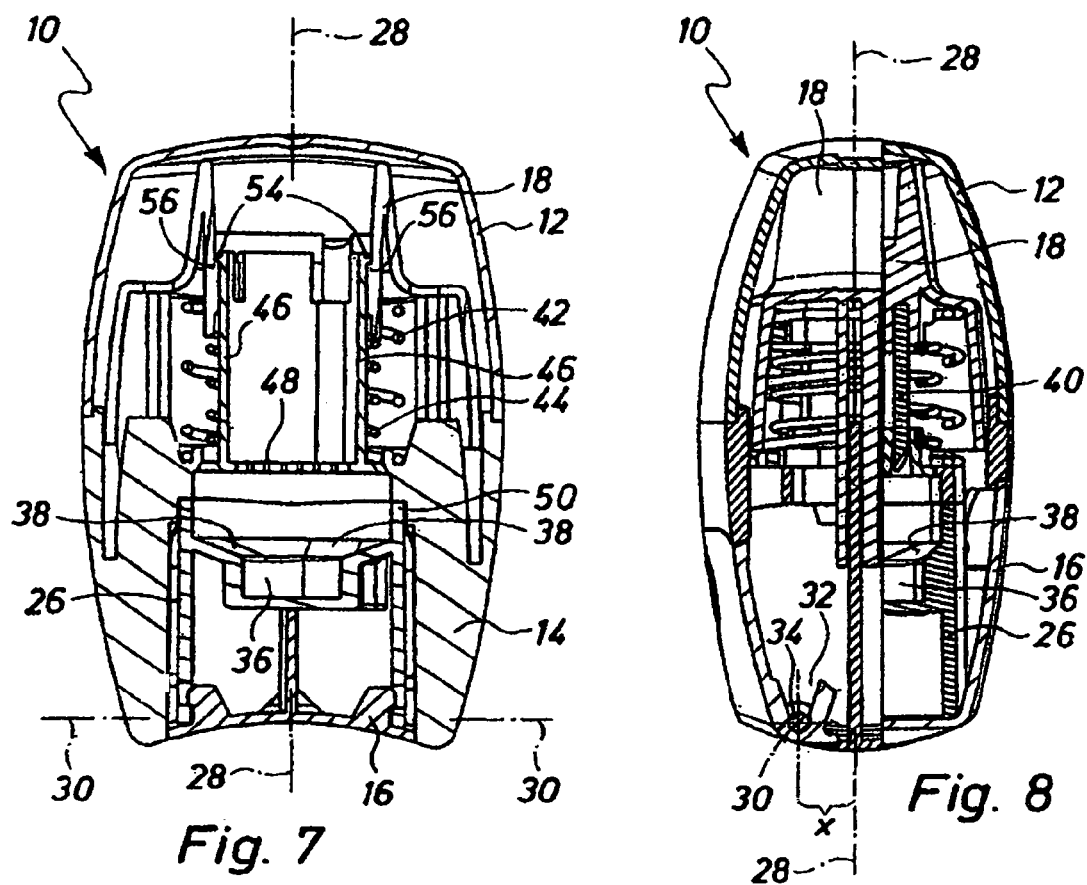

As can be seen from FIGS. 7 and 8 in particular, the pivoting element 16 is arranged spaced apart from a pivot axis 30, which is offset by the value x from the center longitudinal axis 28 of the base housing, or respectively of the mouthpiece. The pivot axis 30 furthermore extends perpendicularly in relation to the center longitudinal axis 28. For a pivotable arrangement, the pivoting element 16 provides pivoting recesses 32, which open in a V-shape, which are engaged by pivoting pins 34 oppositely located on the base housing 14 and facing each other.

Figure 6:
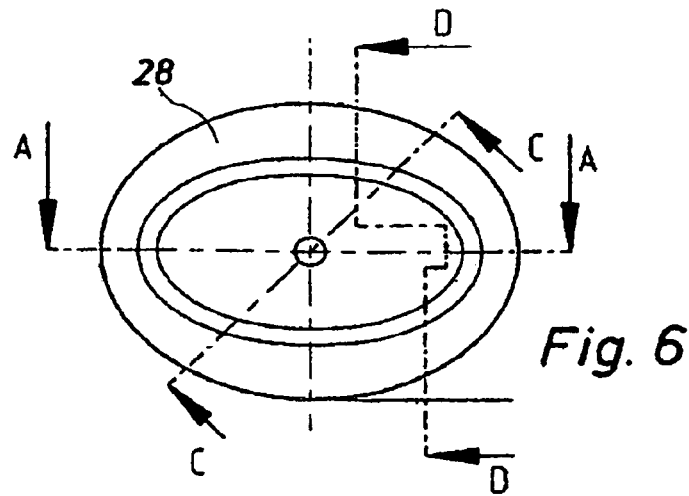

It becomes clear from the sectional views in FIGS. 7, 8, 9 and 10 in particular that the capsule receptacle 26, which is fastened on the pivoting element 16, has a depression 36, which is embodied substantially slightly larger than the capsule to be received, which is followed by surfaces 38 extending in a funnel shape toward the depression. In this case the depression 36 extends obliquely in relation to the center longitudinal planes of the narrow side and of the broad side of the base housing and of the mouthpiece, wherein the section line A-A in FIG. 6 extends along the center longitudinal plane of the broad side of the base housing 14, or respectively of the inhaler 10. This also becomes clear from FIG. 5 in particular. The section line C-C in accordance with FIG. 6 represented in FIG. 9 extends along the longitudinal direction of the depression.

Figure 9:
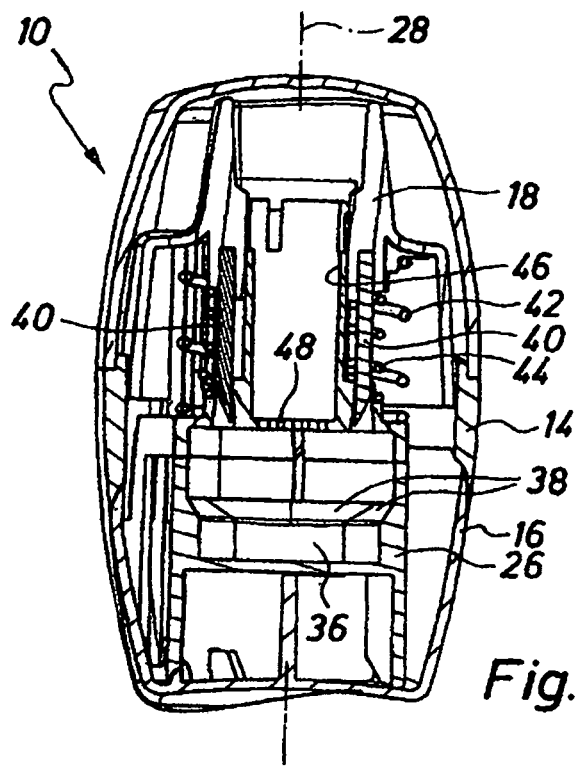
Figure 10:
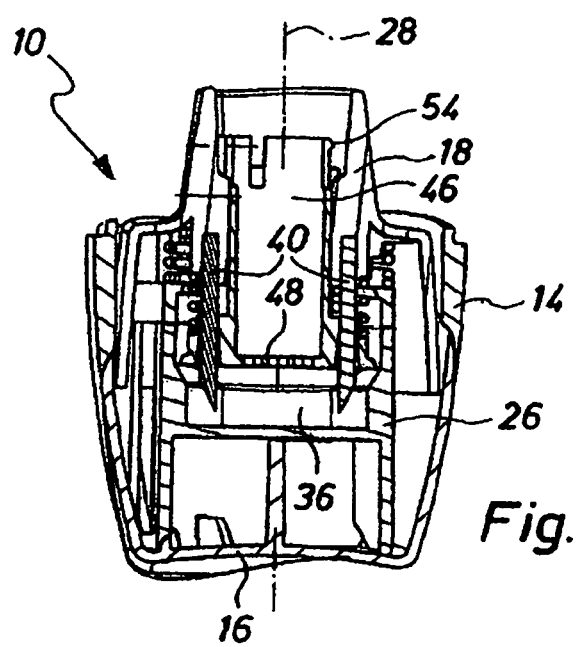

It becomes clear from FIGS. 9 and 10 that two opening means in the form of needles 40 extending in the longitudinal direction are arranged on the mouthpiece 18. Together with the needles 40, the mouthpiece 18 can be pressed down along the longitudinal axis 28 toward the base housing. FIG. 9 shows the normal position of the mouthpiece 18, and FIG. 10 the pressed-down opened position of the mouthpiece 18. In the pressed-down position, the needles 40 protrude into the capsule receptacle 26, as well as into the depression 36 of the capsule receptacle 26. A capsule present in the capsule receptacle 26 is thus perforated, or respectively opened, when the mouthpiece 18 is pressed down. Two spring elements 42, 44 are provided between the base housing 14 and the mouthpiece 18 which, in the normal position, act on the mouthpiece with prestress. Thus, pressing-down on the mouthpiece 18 takes place opposite the prestressing force of the two spring elements 42, 44. In the exemplary embodiment in accordance with the drawing figures, two spring elements 42, 44 in the form of helical springs are provided, which are arranged extending coaxially in respect to each other around the center longitudinal axis 28. Because of providing these two spring elements, a uniform action on the mouthpiece 18 for movement from the opening position into the normal position is achieved. Tilting or jamming of the mouthpiece 18 in the course of the movement from the opening position into the normal position is hereby counteracted.

The mouthpiece 18 as such is guided by a sleeve-like intermediate element 46 arranged on the base housing 14. The intermediate element 46 is embodied to be hollow and closes off the capsule receptacle 26 in the direction toward the mouthpiece 18 by means of a sieve-like structure 48. This has the advantage that, in the course of retracting the needles 40, the capsule, which has possibly been carried along by the needles 40, is pushed off at the intermediate element 46, or respectively the structure 48, and falls back into the capsule receptacle 26. Also, the capsule remains in the capsule receptacle 26 in the course of inhaling through the mouthpiece 18, when air from the capsule receptacle 26 is aspirated via the intermediate element 46 and the mouthpiece 18.

For securing the mouthpiece 18 in the normal position against the spring force of the spring elements 42, 44, radially outwardly projecting retaining protrusions 54 are provided on the sieve-like structure 48 of the intermediate element 46. These retaining protrusions 54, which can be seen in particular in FIG. 7, work together with radially inwardly protruding retaining sections 56 provided on the mouthpiece 18.

In order to make possible the inflow of air into the capsule receptacle 26 for inhaling, even in the pivoted-in state of the pivoting element 16, the capsule receptacle has a suction inlet 52, which can be easily seen in FIG. 5, on its substantially perfectly circular upper edge 50.

The sequence when using the inhaler 10 represented in the drawing figures is as follows: in accordance with FIGS. 4 and 5, the pivoting element 16 is initially pivoted out of the base housing 14. A dry capsule is subsequently placed into the capsule receptacle 26 and the pivoting element is pivoted into the base housing. Because of the surfaces 38 which, in the pivoted-in state, extend funnel-like obliquely downward, the capsule gets automatically into the depression 36. Thereafter, for opening the capsule, the mouthpiece 18 is pressed axially downward against the force of the springs 42, 44, as represented in FIG. 10. In the process, the needles 40 open the capsule. In the course of the automatic retraction of the mouthpiece by means of the spring elements 42, 44, the capsule is pushed off the intermediate element 46 and falls back into the capsule receptacle 26. Thereafter, the powder can be inhaled by placing the mouth on the mouthpiece 18 and subsequently sucking in air. In the process, the powder present in the capsule receptacle 26 is inhaled, together with the aspirated air, through the sieve structure 48, the interior of the intermediate element 46 and the interior of the mouthpiece 18. The pivoting element 16 can subsequently be pivoted out of the base housing 14, and the empty capsule can be removed from the capsule receptacle 26 and recycled.

For the storage of capsules to be used later, the capsule receptacle can house a storage space, not represented in the drawing figures. Because of this it is possible to take along a certain supply in the inhaler. In this case the storage space is accessible, in particular with the capsule receptacle pivoted out, for the insertion, or respectively removal, of capsules to be stored, or respectively already stored, and is not accessible when the capsule receptacle is pivoted in.

FIGS. 11 and 12 show a variation of the inhaler 10, which is represented inverted in FIG. 11, in which the pivoting element 16 is provided with two openings 58 which lead to a storage space and are closed by a cap 60, which is displaceably conducted on the underside 22. As represented by the two-headed arrow 62, the cap 60 can be displaced in two directions in such a way that respectively one of the openings 58 is freed, so that a capsule 64 can be removed. The cap 60 has detents or snap-in knobs, by means of which it is maintained in the closed position, in which both openings 58 are closed, and in the two opening positions. The cap 60 can be provided on its top with slightly protruding strips 66, which make the displacement of the cap, for example by means of the thumb, easier.

FIG. 12 shows the pivoting element 16 in the pivoted position and with the cap 60 pulled off, from which two capsules 84 can be removed one after the other. A magazine 68 for receiving a capsule 64 is connected with the one opening 58. It is also conceivable that a magazine for receiving several capsules be provided in the pivoting element 16, which can then be dispensed through a single opening 58 by means of a dispenser, not represented.

We claim:

1. A dry powder inhaler for a capsule containing dry powder, the inhaler comprising: a base housing; a mouthpiece, through which the dry powder can be inhaled from an opened capsule, wherein said mouthpiece can be moved relative to said base housing from a normal mouthpiece position into an opening mouthpiece position to open the capsule; at least one needle- or blade-like opening means fastened to said mouthpiece to open the capsule when said mouthpiece is moved into said opening mouthpiece position; and a pivoting element cooperating with said base housing on a side thereof facing away from said mouthpiece, said pivoting element comprising or supporting a capsule receptacle, said pivoting element structured to pivot relative to said base housing about a pivot axis extending perpendicularly with respect to a center longitudinal axis of said mouthpiece or of said base housing, wherein, in a closed non-pivoted normal pivoting element position, the pivoting element is substantially flush with an exterior of said base housing, at least portions of said pivoting element pivoting out of said base housing for insertion of the capsule into said capsule receptacle, said inhaler further comprising a spring element disposed between said base housing and said mouthpiece to maintain said mouthpiece under prestress in said normal mouthpiece position.

2. The dry powder inhaler of claim 1, further comprising a substantially sleeve-like intermediate element disposed on the base housing for guiding said mouthpiece, wherein, when inhaling, said intermediate element conducts the dry powder from the capsule receptacle to said mouthpiece, said intermediate element having a sieve structure on a side facing said capsule receptacle.

3. The dry powder inhaler of claim 2, further comprising a spring element disposed between said base housing and said mouthpiece to maintain said mouthpiece in said normal mouthpiece position under prestress, wherein said spring element automatically returns said mouthpiece from said opening mouthpiece position into said normal mouthpiece position, the capsule being stripped off at said sieve structure, so that the capsule falls back into said capsule receptacle.

4. The dry powder inhaler of claim 3, further comprising an addition spring element disposed between said mouthpiece and said intermediate element.

5. The dry powder inhaler of claim 1, wherein said opening means comprises at least one needle extending in a longitudinal direction of said mouthpiece.

6. The dry powder inhaler of claim 1, wherein said pivot axis is arranged offset with respect to said center longitudinal axis of said mouthpiece or of said base housing.

7. The dry powder inhaler of claim 1 wherein said capsule receptacle is delimited by a substantially circular upper edge.

8. The dry powder inhaler of claim 1, wherein said pivoting element has a storage space for storing capsules.

9. The dry powder of claim 8, wherein, when said capsule receptacle is pivoted-out, said storage space is accessible for introduction or removal of capsules and when said capsule receptacle is pivoted-in, said storage space is not accessible.

10. A dry powder inhaler for a capsule containing dry powder, the inhaler comprising: a base housing; a mouthpiece, through which the dry powder can be inhaled from an opened capsule, wherein said mouthpiece calf be moved relative to said base housing from a normal mouthpiece position into an opening mouthpiece position to open the capsule; at least one needle- or blade-like opening means fastened to said mouthpiece to open the capsule when said mouthpiece is moved into said opening mouthpiece position; and a pivoting element cooperating with said base housing on a side thereof facing away from said mouthpiece, said pivoting element comprising or supporting a capsule receptacle, said pivoting element structured to pivot relative to said base housing about a pivot axis extending perpendicularly with respect to a center longitudinal axis of said mouthpiece or of said base housing, wherein, in a closed non-pivoted normal pivoting element position, the pivoting element is substantially flush with an exterior of said base housing, at least portions of said pivoting element pivoting out of said base housing for insertion of the capsule into said capsule receptacle; and wherein, in a lateral view thereof, said pivoting element has a U-shaped exterior contour which extends from a front over a underside as far as a back of said base housing.

11. The dry powder inhaler of claim 10, wherein said capsule receptacle is arranged between two U-legs of said pivoting element.

12. The dry powder inhaler of claim 10, wherein said capsule receptacle is delimited by a substantially circular upper edge.

13. The dry powder inhaler of claim 10, wherein said pivoting element has a storage space for storing capsules.

14. The dry powder inhaler of claim 10, wherein said capsule receptacle is arranged between two V-legs of said pivoting element.

15. A dry powder inhaler for a capsule containing dry powder, the inhaler comprising: a base housing; a mouthpiece, through which the dry powder can be inhaled from an opened capsule, wherein said mouthpiece can be moved relative to said base housing from a normal mouthpiece position into an opening mouthpiece position to open the capsule; at least one needle-or blade-like opening means fastened to said mouthpiece to open the capsule when said mouthpiece is moved into said opening mouthpiece position; and a pivoting element cooperating with said base housing on a side thereof facing away from said mouthpiece, said pivoting element comprising or supporting a capsule receptacle, said pivoting element structured to, pivot relative to said base housing about a pivot axis extending perpendicularly with respect to a center longitudinal axis of said mouthpiece or of said base housing, wherein, in a closed non-pivoted normal pivoting element position, the pivoting element is substantially flush with an exterior of said base housing, at least portions of said pivoting element pivoting out of said base housing for insertion of the capsule into said capsule receptacle; wherein said capsule receptacle has a depression which is slightly larger than the capsule, said capsule receptacle also having surfaces extending in a funnel-like manner towards said depression; and wherein said pivoting element has at least one suction inlet for suctioning during inhalation, said suction inlet disposed proximate an upper edge of said pivoting element.

16. The dry powder inhaler of claim 15, wherein said capsule receptacle is delimited by a substantially circular upper edge.

17. The dry powder inhaler of claim 15, wherein said pivoting element has a storage space for storing capsules.

18. The dry powder inhaler of claim 15, wherein a longitudinal axis of said depression extends obliquely relative to a center longitudinal plane of said base housing.

\* \* \* \* \*